US 6,284,792 B1

(12) United States Patent
Koller et al.

(10) Patent No.: US 6,284,792 B1
(45) Date of Patent: Sep. 4, 2001

(54) FORMULATION OF VALNEMULIN

(75) Inventors: Kurt Koller, Innsbruck; Franz Schwarz, Wörgl, both of (AT)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/733,477

(22) Filed: Dec. 8, 2000

(30) Foreign Application Priority Data

Dec. 9, 1999 (EP) .................................... 99811128

(51) Int. Cl.⁷ ........................................ A61K 31/22
(52) U.S. Cl. ................................................. 514/550
(58) Field of Search ............................................. 514/550

(56) References Cited

U.S. PATENT DOCUMENTS 5,164,526 * 11/1992 Macher ................................... 560/16
6,130,250 * 10/2000 Burch et al. ......................... 514/550

FOREIGN PATENT DOCUMENTS

WO 98/01127  7/1997 (WO).

* cited by examiner

Primary Examiner—Raymond Henley, III
(74) Attorney, Agent, or Firm—Michael U. Lee

(57) ABSTRACT

The preparation of an improved galenic delivery form of valnemulin, which is notable for its good tolerance and stability in storage, is described. The new delivery form in question is a non-aqueous or oily injection formulation, which is obtainable by means of in-situ preparation and subsequent stabilisation of the free, relatively unstable base of the active ingredient. A further aspect of the present invention concerns the usage of such an injection formulation in a method of treating infectious diseases in productive livestock or domestic animals.

12 Claims, No Drawings

FORMULATION OF VALNEMULIN

NEW FORMULATION

The present invention relates to the preparation of an improved galenic delivery form of valnemulin, which is notable for its good tolerance and stability in storage. The new delivery form in question is a non-aqueous or oily injection formulation, which is obtainable by means of in-situ preparation and subsequent stabilisation of the free, relatively unstable base of the active ingredient. A further aspect of the present invention concerns the oily injection formulation as such and its usage in a method of treating infectious diseases in productive livestock or domestic animals.

In connection with the present invention, valnemulin is understood to be the compound shown in the following formula I (I)

[Chemical structure of Valnemulin]

Valnemulin

Valnemulin is known from EP-0.1 53.277 and is described specifically therein in example 12. Valnemulin is also known by the commercial name Econor®.

As is generally known, this compound has antibacterial properties, e.g. following oral or parenteral administration, and is used for the prevention or cure of a series of bacterial infections in the field of animal health. The broad spectrum of activity includes *Streptococcus aronson, Staphylococcus aureus, Mycoplasma arthritidis, Mycoplasma bovigenitalium, Mycoplasma bovimastitidis, Mycoplasma bovirhinis,* Mycoplasma sp., *Mycoplasma canis, Mycoplasma felis, Mycoplasma fermentans, Mycoplasma gallinarum, Mycoplasma gallisepticum, A. granularum, Mycoplasma hominis, Mydoplasma hyorhinis, Actinobacillus laidlawii, Mycoplasma meleagridis, Mycoplasma neurolyticum, Mycoplasma pneumonia* and *Mycoplasma hyopneumoniae.*

WO 98/01127 describes its excellent activity against an illness complex that can arise whenever animals are kept in a very restricted space (increased stocking density) e.g. for transport purposes, and are thus exposed to great stress. The most frequent pathogens that play a decisive role in this instance are *Mycoplasma hyopneumoniae, Serpulina* (formerly Treponema) *hyodysenteriae, Serpulina pilosicoli, Lawsonia intracellularis, Mycoplasma gamlisepticum, Pasteurella multocida, Actinobacilius* (Haemophilus) *pleuropneumoniae* and *Haemophilus parasuis,* whereby diseases of the respiratory tract and other infections often occur together and lead to a complex clinical picture. All herd animals are affected, e.g. cattle, sheep and pigs, but also poultry.

In its free form (valnemulin base), valnemulin is relatively unstable and is therefore primarily used in the form of its salts, particularly as the hydrochloride. A current method of administering antibiotics in the field of animal health is the injection, since it is suitable for administering a controlled single dose and thus a quantity tailored to individual needs. This is often crucial to successful control of many infectious diseases in the field of animal medicines. In contrast, oral administration cannot be controlled nearly so well, and is more customary in human medicine.

However, it has been shown that aqueous injection solutions and even oily injection suspensions of the salts of valnemulin are poorly tolerated by most domestic animals and in particular by pigs. Damage ranging from mild skin irritation to poorly healing necroses, has been observed. This is also one of the reasons that valnemulin has mainly been used orally until now. In addition, aqueous solutions usually do not show the desired depot action. A further problem is that valnemulin cannot be produced in technical quantities in the free form, as the so-called valnemulin base, but occurs as the salt, and has therefore been used for therapy as the salt.

However, for commercial usage, it would be extremely desirable to have stable, storable, oily and, in addition, tolerable injection preparations.

It has now surprisingly been found that chemically stable, non-aqueous injection preparations of valnemulin can be produced in situ and can be stabilised in non-aqueous or oily solvents.

Suitable non-aqueous or oily solvents (i) for the in situ production of the valnemulin free base in connection with the present invention are isopropyl myristate, semi-synthetic and synthetic esters of glycerol, or ethylene or propylene glycol with short-chained to medium-chained mono- or dicarboxylic acids, for example mono-, di- and triglycerides (e.g. neutral oils or miglyol).

In order to stabilise the free base, other solvents (ii) are added to these solvents (i), e.g. esters of medium-hained to long-chained carboxylic acids (e.g. lactic, lauric, myristic, palmitic, stearic and oleic acid etc.) with monovalent alcohols (e.g. ethanol, n-propanol, 2-propanol, etc.), 1,2-O-isopropylidene glycerol, glycerol, ethanol, N,N-dimethylacetamide, benzyl benzoate or tetraethylene glycol, so that mixtures (iii) of solvents (i) with solvents (ii) are present in the end product. The addition of solvents (ii) serves to improve the galenic properties. Especially preferred as solvent (i) is isopropyl myristate with the addition of solvent (ii) benzyl benzoate or ethanol.

A preferred embodiment of the present invention is notable for the fact that solvents (I) and (ii) are present in the end product in a ratio of ca. 70:15.

As already mentioned, the free base of valnemulin has until now not been obtainable on a large scale. Therefore, in the following, a new and surprising way is shown of preparing this free base in situ and formulating it in a stable form.

To this end, 0.5 to 30% by weight, preferably 5 to 10% by weight of a salt of valnemulin is suspended in a non-aqueous solvent (i) in a concentration range of 50 to 99% by weight. Appropriate alkaline excipients are added to the suspension whilst stirring and heating gently at a temperature ranging from ca. 50 to 80° C., in order to release the valnemulin base in situ, whereby the free base immediately dissolves in the solvent (i).

Suitable alkaline excipients for the in situ release of the free valnemulin base are, for example, alkali and alkaline earth carbonates, hydrogen carbonates and hydroxides, or organic amines, such as triethylamine.

After completion of this process, the two phases which are immiscible together, the aqueous and the non-aqueous phase, are separated from one another at a temperature of ca. 50 to ca. 80° C. This phase separation may be assisted by centrifuging. The separated non-aqueous phase, which now contains the free base of (I), is washed many times with water at room temperature and undergoes fresh phase separation at a temperature of ca. 50 to 80° C. The non-aqueous phase is subsequently dried e.g. using a vacuum, in order to remove residual water and volatile substances such as organic amines, and is mixed with a solvent or solvent mixture from group (ii) to stabilise it. This addition of (ii) improves the galenic properties of the formulations.

To stabilise against oxidising influences, physiologically acceptable antioxidants may be added to the solution obtained, e.g. esters of ascorbic acid, butyl hydroxy toluene, butyl hydroxy anisole, propyl gallate, tocopherols or tocopherol derivatives, etc., and to stabilise against microbial infestation, physiologically acceptable preservatives may be added, e.g. benzyl alcohol, chlorocresol, chlorobutanol, esters of parahydroxybenzoic acid, phenoxy-ethanol, phenol and phenol derivatives, sorbic acd, etc.

The finished solutions are sterile-filtered or sterilised in the final container, e.g. in ampoules.

The present invention thus comprises essentially the following preferred aspects:

A method of producing a non-aqueous injection formulation which contains as active ingredient the free valnemulin base, optionally a stabiliser to protect against oxidising influences, and likewise optionally a stabiliser to protect against microbial infestation, and which is characterised in that the free valnemulin base is produced in situ from a salt form in a physiologically acceptable non-aqueous solvent or solvent mixture from the above-mentioned category (i) and is stabilised by adding a further solvent from the above-mentioned category (ii).

A preferred embodiment is characterised in that 0.5 to 30% by weight of a salt of valnemulin in a physiologically acceptable non-aqueous solvent or solvent mixture of the above-mentioned category (i) is released in situ whilst heating gently and adding an appropriate alkaline excipient.

Preferably one or more solvents are used as the non-aqueous solvent or solvent mixture from the above-mentioned category (i), these being selected from the series isopropyl myristate, semi-synthetic and synthetic esters of glycerol, or ethylene or propylene glycol with short-chained to medium-chained mono- or dicarboxylic acids, medium-chained to long-chained carboxylic acids with monovalent alcohols.

A further notable embodiment is characterised in that a salt of valnemulin is suspended in a solvent in a concentration range of 50 to 99% by weight, and the free base of valnemulin is produced in situ using an appropriate alkaline excipient, whilst heating gently and stirring.

In a preferred variant of the process, to physically stabilise the valnemulin base, an ester of medium-chained to long-chained carboxylic acids with monovalent alcohols, 1,2-O-isopropylidene glycerol, glycerol, ethanol, N,N-dimethylacetamide, benzyl benzoate or tetra-ethylene glycol is added as a stabilising solvent of the above-mentioned category (ii).

In the preferred embodiments, solvents (i) and (ii) are present in the end product in a ratio of ca. 70:15.

An especially preferred variant of the process is characterised in that a salt of valnemulin is suspended in a solvent or solvent mixture (i), an appropriate alkaline excipient is added to the suspension whilst stirring and heating gently in the range of ca. 50 to ca. 80° C. in order to effect in situ release of the valnemulin base, the resulting free base being absorbed by this solvent (i); after completion of this process, the two phases which are immiscible together, the aqueous and the non-aqueous phase, are separated from one another at a temperature of ca. 50 to ca. 80° C.; the separated non-aqueous phase, which now contains the free base of (I), is washed many times with water at room temperature and undergoes fresh phase separation at a temperature of ca. 50 to 80° C.; the non-aqueous phase is subsequently dried and volatile components are removed, and it is mixed with a solvent or solvent mixture from group (ii) to stabilise it A further object of the present invention is formed by an oily, stabilised injection formulation, containing as active ingredient the free valnemulin base, which is obtainable by one of the above-characterised releasing and stabilising processes. The present invention also includes the usage of the described oily injection formulation in a method of treating infectious diseases of productive livestock or domestic animals.

FORMULATION EXAMPLES

Example 1

Injection Formulations

Each 100 ml of the ready injection formulation contains 5 g of valnemulin base. The amounts of grams indicated before the parenthesis (formulation 1: 90.0 g, formulation 2: 85.0 g and formulation 3: 86.0 g) are a result of the different densities of the mixtures of isopropyl myristate, ethanol and benzyl benzoate. The reason for giving two figures lies in the preparation, since the ingredients are weighed in grams, but volumetric (ml) amounts are measured in.

| Formulation 1 | g |
|---|---|
| valnemulin | 5.0 |
| benzyl benzoate | 15.1 |
| isopropyl myristate | 69.9 |
| | 90.0 (100.0 ml) |
| Formulation 2 | g |
| valnemulin | 5.0 |
| ethanol | 13.5 |
| isopropyl myristate | 66.5 |
| | 85.0 (100.0 ml) |
| Formulation 3 | g |
| valnemulin | 5.0 |
| isopropyl myristate | 81.0 |
| | 86.0 (100.0 ml) |

Chemical Stability Data

| | Stability of an oily injection solution of valnemulin in %: | | | | | |
|---|---|---|---|---|---|---|
| valnemulin | 25° C./60% relative humidity | | | 40° C./75% relative humidity | | |
| content after | form. 1 | form. 2 | form. 3 | form. 1 | form. 2 | form. 3 |
| 0 months | 99.2 | 99.8 | 98.5 | 99.2 | 99.8 | 98.5 |
| 1 month[11] | 99.9 | 99.2 | 98.9 | 99.7 | 100.4 | 98.4 |
| 2 months | 100.2 | 100.5 | 100.3 | 99.4 | 100.4 | 99.4 |
| 3 months | 101.2 | 102.0 | 99.6 | 100.2 | 101.2 | 100.8 |
| 6 months | 101.4 | 100.4 | n.a. | 98.9 | 99.2 | n.a. | n.a. indicates not tested. Values greater than 100% result from deviations in the analysis method.

All three formulations proved to be chemically stable.

Stability of an oily suspension of valnemulin hydrochloride in %:

| valnemulin content after | 25° C./60% relative humidity | 40° C./75% relative humidity |
|---|---|---|
| 0 weeks | 102.0 | 102.0 |
| 8 weeks | 104.8 | 102.8 |

Values greater than 100% result from deviations in the analysis method.

Tolerance Data

An investigation of tolerance was made by means of an intramuscular injection of the injection formulation to pigs and evaluating its effect on the adjacent tissue.

| | diameter of necrosis in cm | | | |
|---|---|---|---|---|
| | formulation 1 | placebo | formulation 2 | placebo |
| neck area | 1 | 0 | 4 | n.a. |
| thigh | 1 | n.a. | 3 | 5 |

The formulations are compared with the placebo. It is shown that the two formulations do not exhibit significantly poorer tolerance than the placebos.

What we claim is:

1. A method of producing a non-aqueous composition comprising a free valnemulin base; wherein the free valnemulin base is produced in situ by contacting a salt of valnemulin with a physiologically acceptable non-aqueous solvent or solvent mixture (i) and is stabilized by adding a further solvent (ii).

2. The method according to claim 1 further comprising contacting the free valnemulin base with a stabilizing agent for protecting the free valnemulin base from oxidation.

3. A method of producing a non-aqueous composition comprising a free valnemulin base; wherein the free valnemulin base is produced in situ by contacting a salt of valnemulin with a physiologically acceptable non-aqueous solvent or solvent mixture (i) and optionally stabilizing the composition by adding a further solvent (ii).

4. The method according to claim 3 in which 0.5 to 30% by weight of the salt of valnemulin is reacted with the physiologically acceptable non-aqueous solvent or solvent mixture (i) to yield the composition in situ in the presence of heat and an alkaline compound.

5. The method according to claim 3 in which the non-aqueous solvent or solvent mixture (i) is selected from one or more solvents of isopropyl myristate, semi-synthetic and synthetic esters cf glycerol, ethylene or propylene glycol with short-chained to medium-chained mono- or dicarboxylic acids, and medium-chained to long-chained carboxylic acids with monovalent alcohols.

6. The method according to claim 4 in which the salt of valnemulin is suspended in a physiologically acceptable non-aqueous solvent or solvent mixture (i) in a concentration range of 50 to 99% by weight, and the free base of valnemulin is produced in situ in the presence of an alkaline compound, heat and stirring.

7. The method according to claim 1 wherein the stabilizing solvent (ii) comprises an ester of medium-chained to long-chained carboxylic acids with monovalent alcohols, 1,2-O-isopropylidene glycerol, glycerol, ethanol, N,N-dimethylacetamide, benzyl benzoate or tetraethylene glycol, or mixture thereof.

8. The method according to claim 1 wherein solvents (i) and (ii) are present in the composition in a ratio of about 70:15.

9. The method of producing a non-aqueous composition comprising suspending a salt of valnemulin in a physiologically acceptable non-aqueous solvent or solvent mixture (i), adding an alkaline compound to the suspension while stirring and heating in a temperature range of about 50° C. to about 80° C. in order to effect in situ release of the valnemulin base in solvent (i), separating the aqueous phase and the non-aqueous phase at a temperature of about 50 to about 80°C.; washing the valnemulin free base-containing non-aqueous phase with water at room temperature to yield a fresh phase separation at a temperature of about 50 to 80° C.; drying the non-aqueous phase and removing volatile components, and mixing the dried non-aqueous phase with a stabilizing solvent or solvent mixture (ii).

10. A composition comprising free valnemulin base obtainable by the method according to claim 1.

11. A composition according to claim 10 in a form suitable for administration to a mammal by injection.

12., The composition according to claim 10 in an amount effective to treat infectious diseases of productive livestock or domestic animals.

\* \* \* \* \*

UNITED STATES PATENT AND TRADEMARK OFFICE
CERTIFICATE OF CORRECTION

PATENT NO. : 6,284,792 B1
DATED : September 4, 2001
INVENTOR(S) : Koller et al.

It is certified that error appears in the above-identified patent and that said Letters Patent is hereby corrected as shown below:

Column 6,
Line 6, change "cf" to -- of --.

Signed and Sealed this

Twenty-fourth Day of December, 2002

JAMES E. ROGAN
*Director of the United States Patent and Trademark Office*